United States Patent
McKay et al.

(10) Patent No.: US 9,902,750 B2
(45) Date of Patent: Feb. 27, 2018

(54) PROCESS FOR PRODUCING A FRUCTOSIDE-CONTAINING PRODUCT

(71) Applicant: Furanix Technologies B.V., Amsterdam (NL)

(72) Inventors: Benjamin McKay, Amsterdam (NL); Ana Sofia Vagueiro De Sousa Dias, Amsterdam (NL); Sarwat Iqbal, Amsterdam (NL); Gerardus Johannes Maria Gruter, Amsterdam (NL); Robert-Jan Van Putten, Amsterdam (NL)

(73) Assignee: Synvina C.V., Amsterdam (NL)

( * ) Notice: Subject to any disclaimer, the term of this patent is extended or adjusted under 35 U.S.C. 154(b) by 0 days.

(21) Appl. No.: 14/895,027

(22) PCT Filed: Jun. 6, 2014

(86) PCT No.: PCT/NL2014/050367
§ 371 (c)(1),
(2) Date: Dec. 1, 2015

(87) PCT Pub. No.: WO2014/196861
PCT Pub. Date: Dec. 11, 2014

(65) Prior Publication Data
US 2016/0130292 A1    May 12, 2016

(30) Foreign Application Priority Data
Jun. 6, 2013 (NL) ................................. 2010924

(51) Int. Cl.
C07H 1/00 (2006.01)
C07H 3/02 (2006.01)
C07H 15/04 (2006.01)
C13K 11/00 (2006.01)

(52) U.S. Cl.
CPC ............... C07H 3/02 (2013.01); C07H 1/00 (2013.01); C07H 15/04 (2013.01); C13K 11/00 (2013.01)

(58) Field of Classification Search
CPC . C07H 1/00; C07H 3/02; C07H 15/04; C07D 307/46; C13K 11/00
USPC .......................................... 536/125; 549/488
See application file for complete search history.

(56) References Cited

U.S. PATENT DOCUMENTS

| | | | |
|---|---|---|---|
| 3,431,253 A | 3/1969 | Parrish | |
| 5,270,177 A | 12/1993 | Ramos Lazcano et al. | |
| 6,013,491 A | 1/2000 | Martinez | |
| 6,660,502 B2 | 12/2003 | Catani et al. | |
| 2007/0122892 A1 | 5/2007 | Andersson et al. | |
| 2010/0006091 A1 | 1/2010 | Lapoujade et al. | |
| 2014/0316161 A1* | 10/2014 | Mullen | C07C 51/00 562/577 |

FOREIGN PATENT DOCUMENTS

| | | | |
|---|---|---|---|
| NL | WO1994/09019 | * | 4/1994 |
| WO | 2006/063220 A | | 6/2006 |
| WO | 2007/104514 A2 | | 9/2007 |
| WO | 2012/091570 A1 | | 7/2012 |

OTHER PUBLICATIONS

Moreau et al. Isomerization of glucose into fructose in the presence of cation-exchanged zeolites and hydrotalcites. Applied Catalysis A: General 193 (2000) 257-264.*
Vuorinen et al. Kinetics of Alkali-Catalyzed Isomerization of D-Glucose and D-Fructose in Ethanol-Water Solutions. Carbohydrates Research 108:23-29, 1982.*
Christopher M. Lew, et al., "One-Pot Synthesis of 5-(Ethoxymethyl)fufural from Glucose Using Sn-BEA and Amberlyst Catalysts", I&EC Research, pp. 5364-5369; Mar. 27, 2012.
Jitian Lu, et al., "Conversion of Fructose into 5-hydroxymethylfurfural (HMF) and Its Derivatives Promoted by Inoraganic Salt in Alcohol"; Carbohydrate Research 350; pp. 20-24, Jan. 5, 2012.
Shunmugavel Saravanamurugan, et al., "Efficient Isomerization of Glucose to Fructose over Zeolites in Consecutive Reactions in Alcohol and Aqueous Media", J. Am. Chem, Soc., 135, pp. 5246-5249; Mar. 18, 2013.
Shunmugavel Saravanamurugan, et al., "Solid Acid Catalyzed Formation of Ethyl Levulinate and Ethyl Gluccopyranoside from Mono- and Disacchardies", Catalysis Communications, 17, pp. 71-76; Oct. 12, 2011.
Hisatoshi Asaoka, "Isomerization of D-Glucose by Disodium Pentasilicate ($Na_2Si_5O_{11}$,$xCH_3OH$,$yH_2O$) in Methanol-Water Solutions", Carbohydrate Research, 137, pp. 99-109; 1985.
Christian P. Canlas, et al., "Glucose to Fructose Isomerization Over Solid Oxide Catalysts," Abstract, 241st ACS National Meeting and Exposition, Mar. 27-31, 2011.

* cited by examiner

*Primary Examiner* — Yih-Horng Shiao
(74) *Attorney, Agent, or Firm* — Hofmann & Baron, LLP

(57) ABSTRACT

A fructoside-containing product is manufactured from a glucose-rich feedstock, in a process where glucose to fructose is isomerized by contacting the glucose-rich feedstock with a basic isomerization catalyst in an alcoholic medium at a temperature of at least 75° C., to yield a fructose-containing product; and where at least part of the fructose-containing product obtained therefrom is reacted with an alcohol in the presence of an acid catalyst to yield a fructoside-containing product.

26 Claims, 1 Drawing Sheet

PROCESS FOR PRODUCING A FRUCTOSIDE-CONTAINING PRODUCT

CROSS-REFERENCE TO RELATED APPLICATIONS

This application is the National Stage of International Application No. PCT/NL2014/050367 filed Jun. 6, 2014, which claims the benefit of Netherlands Application No. NL 2010924, filed Jun. 6, 2013, the contents of which is incorporated by reference herein.

FIELD OF THE INVENTION

The present invention relates to a process for producing a fructoside-containing product from a glucose-rich feedstock, comprising isomerizing glucose to fructose.

BACKGROUND OF THE INVENTION

Carbohydrates have increased in importance as bio-based starting materials for a wide range of chemicals. One development is the conversion of carbohydrates to 5-hydroxymethyl furfural and ethers and esters thereof. A process for the conversion to an ether derivative has been described in WO 2007/104514. According to this process a fructose and/or glucose-containing starting material is converted to an ether derivative of 5-hydroxymethylfurfural by reacting the starting material with an alcohol in the presence of an acid catalyst. WO 2012/091570 describes that in order to increase the concentration of the starting material in the feed stream of the process it is beneficial to convert the carbohydrates to a glycoside before being converted to the ether. From this document it is also apparent that the solubility of glucose is lower than that of fructose in the reactant medium, which includes an alcohol.

It would therefore be advantageous if it were possible to provide a process with a high level of fructose that could be used in the process for the production of derivatives of 5-hydroxymethylfurfural.

The process for the provision of a fructose-rich product is known in the prior art. In US 2010/0006091 a process is disclosed wherein a sweet fruit juice is clarified and demineralized and the product thus obtained is then processed to hydrolyse sucrose into fructose and glucose. The fructose is separated from the glucose. The glucose is subsequently isomerized to fructose, and the two fructose fractions are combined. According to the document the isomerization of glucose is achieved using an enzyme with glucose isomerase activity. In this known process the isomerization is conducted in an aqueous environment. This results in a product that becomes available in a significant amount of water. However, if the fructose produced is to be used in a non-aqueous environment the water content becomes a drawback, as the water is then to be removed. Removal of this water can be accomplished by evaporation, but such evaporation adds considerably to costs. Therefore, the process for the production of ethers of 5-hydroxymethylfurfural as described in WO 2007/104514 would benefit if the starting materials would be available in an alcoholic medium. Since the activity of many enzymes is negatively affected in alcoholic mediums, the process according to US 2010/0006091 is not suitable for the intended purpose.

In U.S. Pat. No. 3,431,253 the isomerization of glucose to fructose over an alumina catalyst has been described. The isomerization is accomplished by contacting a solution of glucose with alumina at temperatures from about 35 to 70° C. At temperatures above 70° C. it is stated that the formation of organic acids occur. Although it is stated in the description of U.S. Pat. No. 3,431,253 that it is possible to use mixed water-lower alcohol solutions, such as 90% methanol, 80% ethanol and 75% propanol solutions, in the examples only 100% aqueous solutions of glucose are contacted with alumina at 50° C.

A similar procedure is described in a journal article by H. Asaoka, Carbohydrate Research 137 (1985) 99-109, wherein the isomerization of glucose to fructose was accomplished in a 80% (v/v) methanol-water solution over a disodium pentasilicate catalyst at 45° C. When ethanol or 1,4-dioxane was used instead of methanol, the results were worse. All attempts with propanol, acetone, acetonitrile and tetrahydrofuran gave unsatisfactory results.

Similar teachings are described in Lew et al., Ind. Eng. Chem. Res., 51 (14) (2012) 5364-5366, disclosing the conversion of glucose to fructose over Sn-containing Lewis acid zeolite beta in ethanol at 90° C. The reaction is conducted in the presence of ion exchange resin Amberlyst 131 which catalyses the reaction of fructose formed to hydroxymethyl furfurural and subsequently to ethoxymethyl furfural. In Chem. Abstr., 2011: 336348 by Canlas et al. the conversion of glucose to fructose over Ti- or Sn-containing Bronsted or Lewis acid zeolites in water or methanol at 100 to 160° C. is described. It is observed that the above-mentioned prior art documents do not relate to the formation of fructosides.

In Saravanamurugan et al., J. Amer. Chem. Soc., 135 (14) (2013) 5246-5249 the isomerization of glucose in methanol over acidic zeolites has been described. The product obtained is stated to yield fructosides, which are subsequently hydrolyzed to fructose. In the article it is shown that basic zeolites yield considerably lower amounts of fructose. Whereas acidic catalysts yield more than 20% fructose, the basic catalysts yield from 4 to 18% fructose.

Thus many documents in the prior art stipulate that the isomerization reaction medium contains water. In contrast therewith, it has now been found that it is not necessary that water is present if the reaction temperature is above 75° C. The solvent may then consist of pure alcohol. If water is absent it has been found that no undue formation of organic acids occurs. It has further been found that when the isomerization reaction is conducted in the presence of a basic catalyst and the fructoside formation is conducted in the presence of an acidic catalyst, the amount of fructoside is enhanced.

SUMMARY OF THE INVENTION

Accordingly, the present invention provides a process for the manufacture of a fructoside-containing product from a glucose-rich feedstock, comprising: isomerizing glucose to fructose, by contacting the glucose-containing feedstock in an alcoholic medium with a basic isomerization catalyst at a temperature of at least 75° C. to yield a fructose-containing product, and reacting at least part of the fructose-containing product obtained therefrom with an alcohol in the presence of an acid catalyst to yield a fructoside-containing product. One of the advantages of the process resides in the fact that in this way a relatively high concentration of fructose and fructosides is obtained that react faster than glucose when the resulting product is used in the conversion to 5-hydroxymethylfurfural and derivatives thereof.

The isomerization reaction is carried out in an alcoholic medium. The alcohol can be any alcohol that is liquid at the prevailing conditions. Suitable alcohols include mono-alcohols, but also diols, such as ethylene glycol or propylene glycol or mixture thereof, may be used. Preferably, the alcohol is a mono-alcohol. The mono-alcohol may be linear branched or cyclic. The cyclic alcohol may be aliphatic or aromatic. The alcohols may comprise from 1 to 20 carbon atoms. Suitably, the alcoholic medium in the isomerization zone comprises an alkanol having from 1 to 8 carbon atoms, preferably having from 1 to 4 carbon atoms, more preferably being methanol.

An additional advantage of the operation in alcohol is that fructose in the reaction mixture may be converted to a fructoside. The solubility of the fructoside in the alcohol is generally greater than the solubility of fructose per se. Moreover, if the glucose-containing feedstock would also contain some fructoside, such fructoside would not influence the conversion of glucose to fructose, since the fructoside does not affect the equilibrium of the isomerization. The alcoholic medium may solely consist of alcohol or a mixture of alcohols. However, in practice the glucose-containing feedstock may comprise water. That implies that the reaction medium also comprises water in addition to the alcohol or mixture of alcohols. Especially to promote the formation of fructosides, the amount of water in a water-alcohol blend is at most 20% (v/v), preferably at most 10% v/v, whereas it is more preferably at most 5% v/v. Since the formation of organic acids is virtually completely prevented when no water is present, the alcoholic medium is, most preferably, water-free, i.e. containing less than 1% v/v of water.

Since the isomerization using an enzyme would be negatively affected by the above-described reaction conditions, the isomerization is conducted in a chemical fashion in the presence of an isomerization catalyst. Many catalysts are known for this reaction. However, these catalysts are used in aqueous environments. Still, many of these catalysts can be used. These catalysts may be homogeneous or heterogeneous, i.e. solid, catalysts. It is believed that the isomerization may be catalysed by a metal coordination mechanism. Therefore, catalysts containing metal ions that are capable of coordination are suitably used as isomerization catalyst. Surprisingly, it has been found that the isomerization catalyst is advantageously a basic catalyst. Many basic salts and solids may be used as isomerization catalyst. Suitable isomerization catalysts are therefore selected from the group consisting of hydrotalcite, alkali-exchanged zeolites, alkaline earth metal oxides, and alkali metal hydroxides, alkali metal alcoholates, borates, borinates and boronates, and alkali metal and alkaline earth metal carbonates. Also alumina, alkali metal and alkaline earth metal aluminates, silica, alkali metal and alkaline earth metal silicates and further aluminium chloride and chromium chloride may be used as isomerization catalyst with coordination capabilities. Suitable catalysts therefore include Na, K, Ca or Mg exchanged zeolite X, Y, A, beta, ZSM-5, ZSM-11 and ZSM-35. Examples of alkali metal-containing homogeneous catalysts include Na and K hydroxide, Na or K methanolate, Na or K ethanolate, Na or K borate, Na or K borinate or Na or K boronate. The amount of catalyst may be varied between wide ranges without affecting the reaction selectivity. Suitable amounts range from 0.01 to 50% wt, based on the weight of the glucose-rich feedstock. The skilled person will realize that the amount may vary within wide ranges. The amounts for homogeneous catalysts may be different from the amounts of heterogeneous catalysts.

The temperature in the isomerization reaction is at least 75° C. Due to the use of a chemical isomerization catalyst the skilled person may have a wider temperature range than for an enzymatic isomerization reaction. Preferably, the isomerization is conducted at a temperature of 75 to 180° C., more preferably from 80 to 150° C., most preferably from 80 to 130° C. The temperature is suitably chosen such that the reaction time is not overly long. The process can be conducted in a batch mode as well as in a continuous mode. When the isomerization is conducted in a continuous mode, the flow velocity is designed such that the average residence time of the glucose-containing feedstock is in the same range as the residence time in a batch mode. Typically, the residence time will be selected from 0.1 to 10 hours, preferably from 0.2 to 5 hours. Although the pressure in the reaction does not play a critical role, it is preferred that the pressure is elevated, more preferably at a level of at least the autogenous pressure at the prevailing temperature. Not only will in this way the alcoholic medium remain in the liquid phase, but also the separation of the isomerized product from the alcoholic solvent can be easily accomplished by flashing by reducing the pressure. Suitably, the pressure of the isomerization reaction ranges from 1 to 60 bar, preferably from 2 to 25 bar, wherein the value may be selected dependent on the temperature and the alcohol used.

The glucose-rich feedstock may originate from a variety of sources. It may be a mixture of glucose and alcohol, optionally containing water. One suitable source is sucrose. By means of hydrolysis the sucrose molecule may be split into a fructose and a glucose moiety. Another suitable source is constituted by other carbohydrates, e.g. starch or cellulose. Examples of known processes have been described in U.S. Pat. Nos. 5,270,177, 6,013,491 and 6,660,502, wherein a biologically active catalyst is used for the conversion of sucrose into glucose and fructose, and US application No. 2007/0122892, wherein succinic acid as a chemical catalyst is used for that purpose. When glucose is recovered by alcoholysis of sucrose, the alcoholysis is suitably carried out at a temperature ranging from 25 to 150° C., preferably, from 40 to 100° C., more preferably from 60 to 80° C. The alcoholysis is preferably carried out in the presence of a acid catalyst, e.g. sulphuric acid. The alcoholic medium may comprise water, suitably up to an amount of 10% wt, based on the weight of the alcohol and the water, preferably up to 5% wt water. More preferably the alcoholic medium is substantially water-free, i.e. comprising at most 1.0% wt of water. The contact time between the sucrose feed and the alcohol is suitably from 0.5 to 6 hr, preferably 0.5 to 1.25 hr. The alcohol in which the alcoholysis takes place is advantageously the same alcohol as the one used in the isomerization of the glucose-rich feedstock. Suitable alcohols include lower alcohols, preferably having from 1 to 8, more preferably from 1 to 4 carbon atoms, most preferably being methanol. The concentration of sucrose may range from 20 to 70% wt, preferably from 40 to 60% wt, based on the combination of sucrose and alcohol. It is understood that the sucrose generally has a low solubility in the alcohol, so that a slurry is subjected to the alcoholysis.

A commercially attractive source for the glucose-rich feedstock is derived from starch, from corn, wheat or potatoes. Via well-known procedures the starch is hydrolysed, usually enzymatically, to yield glucose. The resulting product may be concentrated to yield e.g. in the case of corn starch hydrolysis the so-called High Fructose Corn Syrup (HFCS). HFCS may contain up to 90% wt fructose. It would be advantageous to convert the remaining glucose in HFCS also to fructose. The present process provides a method for doing so. The fructose is either removed or converted to fructoside. Subsequently, the remaining product, which is either a fructose-depleted product or a fructoside-product, is subjected to the process according to the present invention, converting at least part of the remaining glucose in the product. Since HFCS is amply available, HFCS is a particularly preferred feedstock for the present process. To the extent that HFCS is contained in water it may be desirable to remove at least part of the water and take up the carbohydrates of the HFCS in the desired alcohol.

The glucose-rich feedstock suitably comprises from 10 to 100% wt glucose, based on the feedstock. The feedstock suitably further comprises fructose, preferably in an amount ranging from 90 to 0% wt, based on the feedstock. The solubility of fructose and glucose in an alcohol is rather limited. To increase the concentration of fructose moieties it is known to convert fructose to fructoside, as is described in e.g. WO 2012/091570. Therefore, the glucose-rich feedstock suitably comprises fructosides. Such feedstock is suitably the product of a reaction of a fructose-containing starting material with an alcohol in the presence of an acid catalyst. Therefore, the glucose-rich feedstock preferably further comprises fructosides obtained from such a reaction. Another suitable compound for use in the glucose-rich feedstock is levoglucosan. Hydrolysis of this compound yields glucose. Especially when the product of the glucose isomerization is subjected to glycoside formation, the levoglucosan may suitably serve as a scavenger for the water that is released in the glycoside formation, and thus may yield glucose, optionally for further isomerization and/or subsequent reactions.

The fructose-containing product obtained in the isomerization process of the present invention is at least partly used in a reaction with an alcohol to form a fructoside. It has been found that the formation of fructosides runs faster than the formation of glucosides. This enables the selective formation of fructosides in a mixture of glucose and fructose. Hence, during the formation of fructosides, the glucose to fructose ratio in any mixture increases. When the reaction product is subsequently subjected to isomerization, the relative excess of glucose will convert into fructose in accordance with the equilibrium that exists at the prevailing isomerization conditions. As already indicated above, it is observed that the fructoside does not interfere in the equilibrium so that a great amount of fructose and fructoside is obtainable.

The fructoside formation reaction is conducted in the presence of an acid catalyst. The reaction conditions may be apparent from WO 2012/091570. The catalyst may be homogeneous, e.g. a mineral acid. Suitable acids include sulphuric acid, phosphoric acid, nitric acid, hydrochloric and hydrobromic acid. Lewis acids may also be used. Organic acids, such as sulphonic and phosphonic acids, may also be used. Examples include methane sulphonic acid, toluene sulphonic acid and methyl phosphonic acid. However, the catalyst may also be, and preferably is, a heterogeneous catalyst, in particular acidic zeolites or acidic ion-exchange resins. Such acidic zeolites may be selected from the group consisting of zeolite X, zeolite Y, zeolite beta, ZSM-5, ZSM-11, ZSM-12, ZSM, 35, ferrierite and combinations thereof, all zeolites preferably being in their H-form. Suitably, the acidic ion-exchange resins include sulphonated polymer resins, e.g. sulphonated styrene-divinylbenzene copolymers, such as the Amberlyst resins (ex Rohm and Haas), and sulphonated tetrafluoroethylene based fluoropolymer-copolymers, such as the Nafion resins (ex DuPont). The reaction conditions suitably include a reaction temperature of 20 to 100° C., preferably, from 30 to 80° C., and a contact time of the glucose-rich feedstock and the alcohol with acid catalyst ranging from 0.1 to 12 hr. At higher temperatures, the selectivity of the conversion to fructosides in preference over the conversion to glucosides, will reduce.

The alcohol that is being selected for the reaction between fructose and the alcohol to fructoside may be selected from a variety of alcohols. However, it is advantageous to select the alcohol such that the solubility of fructoside, fructose and glucose is optimal. Therefore, the alcohol is suitably selected from mono-alcohols that contain from 1 to 8 carbon atoms. Preferably, the alcohol in the conversion zone is selected from $C_1$ to $C_4$ alkanols, more preferably is methanol. It is convenient to use the same alcohol in the reaction of fructose to fructoside as in the alcoholic medium of the isomerization process.

The isomerization reaction and the fructoside formation may be carried out in a single pot. The reactions may be carried out subsequently or simultaneously. When the reactions are carried out simultaneously, the catalysts are suitably heterogeneous and are separated from each other. In such a case the catalysts may be contained is separate bades or baskets, and the reaction mixture may be circulated around the catalysts. A more suitable option is to conduct the reactions subsequently. The catalysts may then be in the same reactor or in separate reactors. It has been found that combination of isomerization of glucose and conversion of fructose to fructoside can be economically used in a process wherein the glucose-rich feedstock is passed to either of the reactions, wherein part of the product of either of reactions is recycled and another part thereof is recovered as the desired fructoside product.

Accordingly, the present invention provides a process for producing a fructoside-rich product from a glucose-rich feedstock, which process comprises the process for isomerising glucose to fructose from a glucose-rich feedstock according to the present invention in an isomerization zone to yield an isomerized product containing fructose, and the process for the manufacture of a fructoside-containing product as described above wherein at least part of the isomerized product containing fructose is reacted with an alcohol in the presence of an acid catalyst in a conversion zone to yield a fructoside-containing conversion product; wherein the glucose-rich feedstock is passed to the isomerization zone or the conversion zone, wherein at least a fraction of the isomerized product is passed to the conversion zone and at least a fraction of the conversion product is passed to the isomerization zone; and wherein either the isomerized product or the conversion product is split into at least two fractions, at least one fraction, i.e. the product fraction, that is split off being recovered as fructoside-rich product.

The latter process provides a process wherein at least a portion of the glucose-rich feedstock is subjected to isomerization. In the isomerization zone glucose is converted into a mixture of glucose and fructose. At least a part of such mixture is subjected to a reaction with an alcohol in the conversion zone. Since fructose is more reactive than glucose, the conversion will mainly result in fructoside. The solubility of fructoside in alcohol is substantially higher than the solubility of fructose in the alcohol. Therefore, the concentration of fructose and glucose moieties in the resulting conversion product may be high. A portion of either the isomerized product or the conversion product is separated from the remainder and recovered as product. At least a portion of the remainder is recycled to the isomerization if the remainder stems from the conversion product, or to the conversion if the remainder stems from the isomerized product.

In this way a solution can be obtained with a satisfactorily high concentration of fructoside, fructose and glucose.

The process according to the present invention may be carried out in a number of ways. Suitable manners to conduct the process include;

- a process, wherein the glucose-rich feedstock is passed to the isomerization zone; substantially the entire isomerized product is passed to the conversion zone; and the conversion product is split into at least two fractions, at least one product fraction that is split off from the conversion product being recovered as fructoside-rich product, and at least another fraction of the conversion product being passed to the isomerization zone;
- a process, wherein the glucose-rich feedstock is passed to the isomerization zone; the isomerized product is split into at least two fractions, at least one product fraction that is split off from the isomerized product being recovered as fructoside-rich product, and at least another fraction of the isomerized product being passed to the conversion zone; and substantially the entire conversion product is passed to the isomerization zone;
- a process, wherein the glucose-rich feedstock is passed to the conversion zone; substantially the entire conversion product is passed to the isomerization zone; and the isomerized product is split into at least two fractions, at least one product fraction that is split off from the isomerized product being recovered as fructoside-rich product, and at least another fraction of the isomerized product being passed to the conversion zone; and
- a process, wherein the glucose-rich feedstock is passed to the conversion zone; the conversion product is split into at least two fractions, at least one product fraction that is split off from the conversion product being recovered as fructoside-rich product, and at least another fraction of the conversion product being passed to the isomerization zone; and substantially the entire isomerized product is passed to the conversion zone.

DETAILED DESCRIPTION OF THE INVENTION

Figure 1:
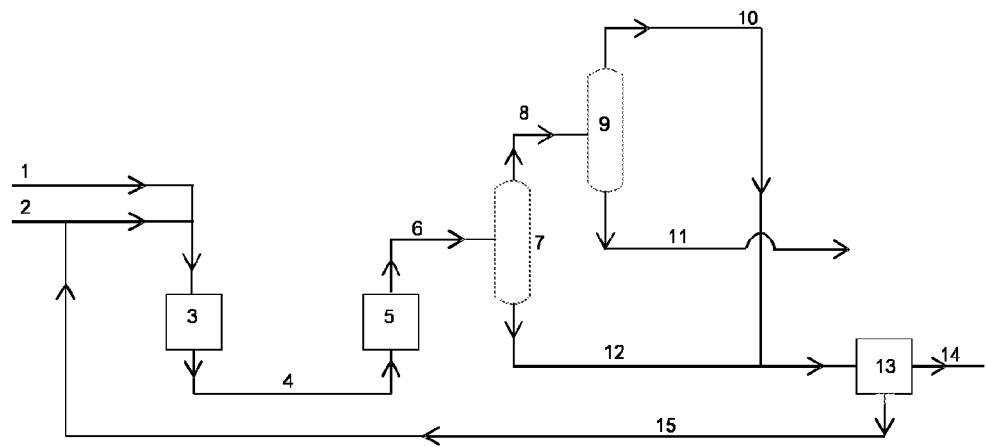
FIGS. 1 and 2 show schematically flow schemes for two embodiments of the process according to the present invention.

An advantage of the present invention is that the reaction is conducted in an alcohol. Whereas the solubility of both fructose and glucose in an alcohol is limited, the solubility of fructoside is higher. Surprisingly, it was found that the presence of fructoside in the alcohol assists in solubilising glucose. Therefore, the conversion of fructose to fructosides enables a higher concentration of glucose and fructose moieties. At the same time any subsequent reaction for which it is preferred not to conduct it in an aqueous environment, e.g. the conversion of these carbohydrates to ethers of 5-hydroxymethylfurfural, can be undertaken without the need of a costly and complicated separation of the aqueous environment that contains fructose and glucose moieties.

The reaction in the conversion zone is carried out under the conditions and with the alcohols as explained above.

In the process of the present invention the conversion product or the isomerized product is split in at least two fractions. Suitably, the split is made into two fractions, one fraction being recycled to the isomerization zone or the conversion zone, as the case may be, and the other fraction being recovered as fructoside product.

During the conversion step water is produced in the formation of fructoside. In order to avoid build-up of water in the system, water is preferably removed during or after the split of the isomerization product or the conversion product. The water removal may suitably be accomplished by flashing, distillation, adsorption or combinations thereof. Other technologies, such as membrane separation techniques, may also be used.

Dependent on the alcohol used, alcohol may be entrained with water when water is being removed. Such may be the case when water removal is effected by flashing or distillation. In such a case, the water fraction that is separated may be subjected to a further separation step to separate the entrained alcohol from water. The alcohol thus separated may be recycled to either of the conversion zone or the isomerization zone.

The glucose-rich feedstock is advantageously passed to the conversion zone or isomerization zone in a liquid form. That implies that the glucose and optionally fructose are dissolved in a suitable solvent. The solvent is commonly water. Since advantageously the level of water is kept at a relatively low level, the concentration of water in the glucose-rich feedstock is preferably at most 5% wt, based on the feedstock, more preferably from 0 to 3% wt. If other solvents are present in the feedstock, such solvents preferably include alcohols, such as those that are used in the conversion zone and/or isomerization zone. When the glucose-rich feedstock is passed into the conversion zone the feedstock preferably already contains fructose. The fructose in the glucose-rich feedstock will react with the alcohol in the conversion zone, yielding fructosides. This embodiment is especially advantageous when the glucose-rich feedstock contains significant amounts of fructose. Therefore, a fructose-rich stream, such as HFCS, constitutes a very suitable feedstock for such embodiments.

The process according to the present invention yields a fructoside-rich product. This product may be recovered as it is produced. It may also in this form be used e.g. in the manufacture of 5-hydroxymethylfurfural or an ether or ester thereof. It may also be advantageous to purify the fructoside-rich product to yield purified fructoside. Such purification may comprise a dewatering step, such as an evaporation or adsorption step. In this way the amount of water in the eventual product can be reduced, which may be beneficial in some further uses.

The invention also provides the use of the fructoside-containing product produced in the process for its manufacture as described above, of the fructoside-rich product produced in the process according to present invention and/or the purified fructoside produced after the above-described purification, as feedstock for the manufacture of 5-hydroxymethylfurfural or for the manufacture of an ether or ester of 5-hydroxymethylfurfural. The manufacture of the desired products may be carried out as described in WO 2007/104514 for the ether product, in WO 2007/104515 for the ester product, and in WO 2006/063220 for 5-hydroxymethyl-furfural. Hence, the present invention also provides a process for the manufacture of 5-hydroxymethylfurfural or an ether or ester thereof, by reacting the fructoside-containing product produced in the process for its manufacture as described above, the fructoside-rich product produced in the process according to present invention and/or the purified fructoside produced after the above-described purification, with an acid catalyst in the presence of a solvent, an alcohol or an organic monocarboxylic acid.

The invention will be further illustrated by means of the figures.

In FIG. 1 a glucose-rich feedstock stream, e.g. an HFCS stream, is introduced in the process via a line 1. An alcohol, e.g. methanol, is introduced into the process via a line 2. The combined glucose-rich feedstock and methanol is passed into a conversion zone 3, wherein fructose, contained in the glucose-rich feedstock, is converted with the alcohol, e.g. methanol into a fructoside. The conversion zone may consist of one or more reactors in series or in parallel. The reactors may be any type of continuous reactors, such as plug flow reactors, trickle flow reactors or continuous stirred tank reactors (CSTRs). Conversion product is withdrawn from the conversion zone 3 via a line 4 and introduced into an isomerization zone 5. The isomerization zone may also contain one or more continuous reactors in series or in parallel, including those mentioned hereinbefore. Isomerized product is withdrawn from the isomerization zone 5 via a line 6 and passed into a flash vessel 7. In the flash vessel water, together with alcohol, is evaporated and withdrawn from the top of the flash vessel via a line 8. The remaining products are discharged from the flash vessel 7 at the bottom via a line 12. The mixture of water and alcohol in line 8 is passed to a separation device, in this case a distillation column 9. Water is separated from the alcohol, and discharged via a line 11 for further treatment or disposal. The alcohol, e.g. methanol, that has a lower boiling point than water, is distilled over the top and passed via a line 10, and is subsequently combined with the products in the line 12. The combined components are fed into a splitter 13, wherein a fraction of the components is separated via a line 14, which is recovered as fructoside-containing product. Another fraction from the splitter 13 is taken away via a line 15, and is subsequently combined with the methanol in the line 2. In this way a portion of the conversion product is recycled to the isomerization zone 3.

Figure 2:
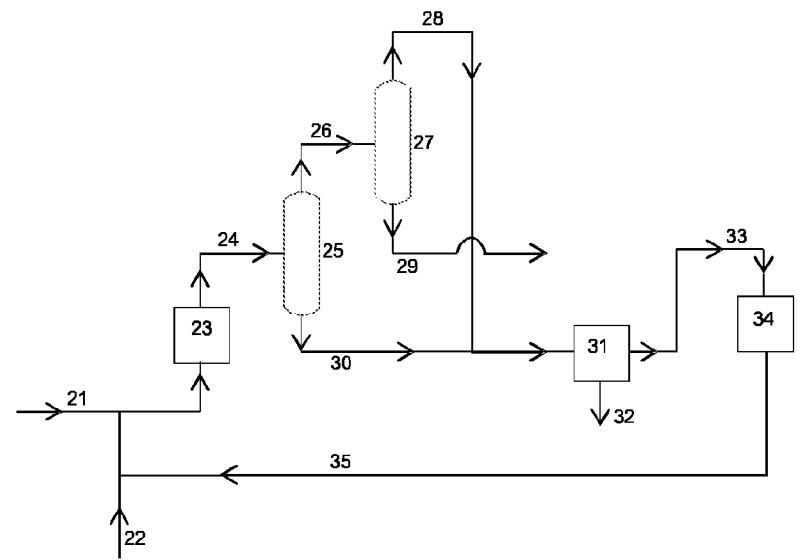

FIG. 2 shows a different embodiment. A glucose-rich feedstock is provided via a line 21. This glucose-rich feedstock may come from e.g. the alcoholysis of sucrose, in particular the methanolysis of sucrose. An alcohol, such as methanol, is provided via a line 22. The alcohol stream is combined with a stream from a line 35. The stream in the line 35 contains fructosides, as will be explained hereinafter. The combination of lines 21, 22 and 35 is fed into an isomerization zone 23. The isomerization zone 23 may consist of one or more reactors. The reactors may be any type of continuous reactors, such as plug flow reactors, trickle flow reactors or CSTRs. Isomerized products are withdrawn from the isomerization zone 23 via a line 24 and passed to a flash vessel 25, where water and alcohol are evaporated and withdrawn via a line 26. The remaining products are discharged via a line 30 at the bottom. The mixture of water and alcohol are separated in a distillation column 27, in a way similar to the one described with relation to FIG. 1. Water that is separated is withdrawn via a line 29 and discharged for disposal or further treatment. Alcohol is withdrawn via a line 28 and combined with the remaining products in the line 30. The combined components are passed to a splitter where the stream is split into a fraction 32 which is recovered as fructoside-containing product, and a fraction 33, that is passed to a conversion zone 34. In the conversion zone 34 fructose from stream 33 is converted to fructoside. The conversion product is withdrawn from the conversion zone 34 via the line 35, thereby providing fructosides that are recovered in the fraction 32 from the splitter 31.

It is evident to the skilled person that the flow schemes do not show any ancillary equipment, such as pumps, compressors, cooling means, control means and re-boiling loops. These ancillary items can be added by the skilled person using common general knowledge.

EXAMPLES

Example 1

In a 7.5 ml batch reactor, 100 mg glucose in 1.00 ml methanol was reacted at 20 bar at temperatures between 80 and 120° C. in the presence of homogeneous base catalysts. Table 1 describes results obtained with different homogeneous catalysts. The amounts of fructose and glucose are expressed as molar percentages, based on the starting amount of glucose.

TABLE 1

| Catalyst | Catalyst concentration (mM) | Temp. (° C.) | Reaction time (min) | Fructose yield (%) | Glucose recovered (%) |
|---|---|---|---|---|---|
| Na$_2$CO$_3$ | 94 | 80 | 60 | 32 | 65 |
| Na$_2$CO$_3$ | 94 | 100 | 15 | 34 | 62 |
| NaOH | 10 | 120 | 30 | 34 | 63 |
| KBO$_2$ | 114 | 120 | 60 | 26 | 62 |

Example 2

Under otherwise identical conditions to example 1, reactions were performed in methanol containing 10% vol water, catalysed with sodium hydroxide. Table 2 describes results obtained from these experiments.

TABLE 2

| Catalyst | Catalyst concentration (mM) | Temperature (° C.) | Reaction time (min) | Fructose yield (%) | Glucose recovered (%) |
|---|---|---|---|---|---|
| NaOH | 10 | 120 | 60 | 24 | 73 |
| NaOH | 25 | 100 | 37.5 | 39 | 47 |
| NaOH | 25 | 80 | 15 | 35 | 55 |

Example 3

Under otherwise identical conditions to example 1, reactions were performed in methanol in the absence of water and at 120° C., and catalysed by heterogeneous bases. Table 3 describes results obtained from these experiments.

TABLE 3

| Catalyst | Catalyst loading (mg) | Reaction time (min) | Fructose yield (%) | Glucose recovered (%) |
|---|---|---|---|---|
| γ Al$_2$O$_3$ | 9.9 | 60 | 14 | 82 |
| MgO | 9.9 | 30 | 20 | 76 |
| MgO | 10 | 60 | 31 | 64 |
| Hydrotalcite | 10.1 | 60 | 21 | 73 |
| MgAlOx | 10.2 | 240 | 37 | 57 |
| Aluminosilicate (X) | 11.6 | 180 | 16 | 79 |

Example 4

In a 7.5 ml batch reactor, approximately 355 mg glucose and 240 mg fructose were reacted in 500 μl methanol at 20 bar at temperatures between 60 and 80° C. in the presence of sulphuric acid as homogeneous acid catalyst. Water content was varied between 0 and 10 wt % relative to the weight of the solvent, that is, methanol and water combined. The total loading of fructose and glucose together is about 60 wt % relative to the weight of the solution. Table 4 describes results at different conditions. The yields on methylfructoside and methylglucoside were quantified and expressed as molar percentages, based on the amounts of fructose and glucose, respectively. Other compounds were not determined.

TABLE 4

| Temperature (° C.) | time (min) | water content (wt %) | $H_2SO_4$ (mM) | methyl fructoside yield (%) | methyl glucoside yield (%) |
|---|---|---|---|---|---|
| 60 | 90 | 0 | 1.2 | 52 | 0.1 |
| 60 | 30 | 0 | 1.2 | 50 | 0 |
| 60 | 30 | 0 | 3.5 | 50 | 0 |
| 60 | 90 | 10 | 3.8 | 34 | 1 |
| 70 | 60 | 0 | 1 | 49 | 0.1 |
| 70 | 60 | 10 | 1 | 35 | 0 |
| 80 | 30 | 0 | 1 | 46 | 0.2 |
| 80 | 30 | 0 | 2.4 | 36 | 0.3 |
| 80 | 30 | 10 | 0.9 | 34 | 0 |

Example 5

Sucrose was subjected to methanolysis by reacting a slurry of 63 wt % sucrose in methanol, containing 5 wt % water and 6 mM $H_2SO_4$, at 60° C. until complete conversion. The products contained more than 43 mol % methylfructosides, more than 16 mol % fructose, about 83 mol % glucose and less than 2.5 mol % of methylglucoside. Other products included about 6 mol % of 5-hydroxymethylfurfural. The molar percentages were based on the molar amount of sucrose. Other by-products were not quantified. The reaction mixture was neutralized with sodium hydroxide.

In a 7.5 ml batch reactor 1.00 ml of this methanolysis product was reacted at 20 bar at temperatures at 80 or 100° C. in the presence of sodium hydroxide as homogeneous base catalyst. Table 5 describes the results.

It is noted that the yields of fructose in Table 5 represent the additional amount of fructose, in addition to the amount that was already present in the feed. This yield is expressed in molar percentage, based on the glucose in the feed.

TABLE 5

| temperature (° C.) | time (min) | water content (wt %) | NaOH concentration (mM) | fructose yield (%) |
|---|---|---|---|---|
| 80 | 60 | 5 | 20 | 5 |
| 100 | 60 | 5 | 15 | 8 |
| 100 | 60 | 5 | 20 | 10 |

The 5-hydroxymethylfurfural and methylglycosides, i.e. the methylfructosides and methylglucosides, were not converted under the isomerization conditions.

The invention claimed is:

1. A process for producing a fructoside-rich product from a glucose-rich feedstock, process consists of comprises isomerizing glucose to fructose from a glucose-rich feedstock by contacting the glucose-rich feedstock in an alcoholic medium with a basic isomerization catalyst at a temperature of at least 75° C., in an isomerization zone to yield an isomerized product containing a mixture of glucose and fructose, and reacting at least part of the isomerized product containing the mixture of glucose and fructose with an alcohol in the presence of an acid catalyst in a conversion zone wherein the alcohol is selected from C1 to C4 alkanols to yield a glucose- and fructoside-containing conversion product, and optionally the step of purifying the fructoside-rich product to yield purified fructoside;
    wherein the glucose-rich feedstock is passed to the isomerization zone or the conversion zone;
    wherein at least a fraction of the isomerized product is passed to the conversion zone and at least a fraction of the conversion product is passed to the isomerization zone; and
    wherein either product from the isomerisation zone or product from the conversion zone is split into at least two fractions, at least one fraction that is split off being recovered as fructoside-rich product.

2. The process according to claim 1, wherein the basic catalyst is selected from the group consisting of hydrotalcite, alkali-exchanged zeolites, alkali metal oxides, alkali metal hydroxides, alkaline earth metal oxides, alkaline earth metal hydroxides, alkali metal alcoholates, alkali metal borates, alkali metal boronates, alkali metal borinates, alkali metal carbonates, alkaline earth metal carbonates and mixtures thereof.

3. The process according to claim 1, wherein the isomerization is conducted at a temperature of 75 to 180° C.

4. The process according to claim 1, wherein the isomerization is conducted at a pressure from 1 to 60 bar.

5. The process according to claim 1, wherein the contact time of the glucose-rich feedstock in the alcoholic medium ranges from 0.1 to 10 hr.

6. The process according to claim 1, wherein the C1 to C4 alkanol is methanol.

7. The process according to claim 1, wherein the at least part of the isomerized product is reacted with the alcohol in the presence of an acid catalyst, selected from the group consisting of acidic zeolites and acidic ion exchange resins.

8. The process according to claim 1, wherein the at least part of the isomerized product is reacted with the alcohol at a temperature of 20 to 100° C.

9. The process according to claim 1, wherein the contact time of the at least part of the isomerized product with the alcohol ranges from 0.1 to 12 hr.

10. The process according to claim 1, wherein the glucose-rich feedstock is passed to the isomerization zone; the at least a fraction of the isomerized product is passed to the conversion zone; and the conversion product is split into at least two fractions, at least one product fraction that is split off from the conversion product being recovered as fructoside-rich product, and at least another fraction of the conversion product being passed to the isomerization zone.

11. The process according to claim 1, wherein the glucose-rich feedstock is passed to the isomerization zone; the isomerized product is split into at least two fractions, at least one product fraction that is split off from the isomerized product being recovered as fructoside-rich product, and at least another fraction of the isomerized product being passed to the conversion zone; and subsequently at least a fraction of the conversion product is passed to the isomerization zone.

12. The process according to claim 1, wherein the glucose-rich feedstock is passed to the conversion zone; subsequently at least a fraction of the conversion product is passed to the isomerization zone; and the isomerized product is split into at least two fractions, at least one product fraction that is split off from the isomerized product being recovered as fructoside-rich product, and at least another fraction of the isomerized product being passed to the conversion zone.

13. The process according to claim 1, wherein the glucose-rich feedstock is passed to the conversion zone; the conversion product is split into at least two fractions, at least one product fraction that is split off from the conversion product being recovered as fructoside-rich product, and at least another fraction of the conversion product being passed to the isomerization zone; and subsequently at least a fraction of the isomerized product is passed to the conversion zone.

14. The process according to claim 1, wherein the split of the isomerization product or the conversion product is into two fractions.

15. The process according to claim 1, wherein before, during or after the split of the isomerization product or the conversion product, water is removed.

16. The process according to claim 15, wherein water is removed by flashing, distillation, adsorption or a combination thereof.

17. The process according to claim 1, wherein the glucose-rich feedstock comprises the reaction product of the alcoholysis of sucrose.

18. The process according to claim 17, wherein the alcoholysis of sucrose is carried out at a temperature ranging from 25 to 150° C.

19. The process according to claim 1, wherein the glucose-rich feedstock is passed to the conversion zone, wherein the glucose-rich feedstock comprises fructose.

20. The process according to claim 19, wherein the glucose-rich feedstock is high fructose corn syrup.

21. The process according to claim 1, wherein the purification comprises a dewatering step.

22. The process according to claim 3, wherein the isomerization is conducted at a temperature of 80 to 150° C.

23. The process according to claim 3, wherein the isomerization is conducted at a temperature of 80 to 130° C.

24. The process according to claim 4, wherein the isomerization is conducted at a pressure of from 2 to 25 bar.

25. The process according to claim 1, wherein the alcoholic medium in the isomerization is methanol.

26. The process according to claim 1, wherein the purification comprises an evaporation or adsorption step.

* * * * *